US009962255B1

(12) United States Patent
Weiss

(10) Patent No.: US 9,962,255 B1
(45) Date of Patent: May 8, 2018

(54) ONE PIECE SELF-LOCKING SCLERAL BUCKLE WITH PLACEMENT INSTRUMENT

(71) Applicant: Jeffrey N. Weiss, Parkland, FL (US)

(72) Inventor: Jeffrey N. Weiss, Parkland, FL (US)

( * ) Notice: Subject to any disclaimer, the term of this patent is extended or adjusted under 35 U.S.C. 154(b) by 0 days. days.

(21) Appl. No.: 13/688,491

(22) Filed: Nov. 29, 2012

Related U.S. Application Data

(63) Continuation-in-part of application No. 09/151,423, filed on Sep. 10, 1998, now abandoned.

(51) Int. Cl.
  *A61F 2/14* (2006.01)
  *A61K 9/00* (2006.01)
  *A61F 9/00* (2006.01)
  *A61F 9/007* (2006.01)

(52) U.S. Cl.
  CPC .............. *A61F 2/14* (2013.01); *A61F 9/0017* (2013.01); *A61F 9/00727* (2013.01); *A61F 2220/0008* (2013.01); *A61F 2250/0007* (2013.01); *A61K 9/0051* (2013.01)

(58) Field of Classification Search
  CPC .......... A61F 2/14; A61F 2/147; A61F 9/0017; A61F 9/007; A61F 9/00727; A61B 2017/12018; A61B 17/122
  USPC ................... 623/4.1, 6.63; 606/151
  See application file for complete search history.

(56) References Cited

U.S. PATENT DOCUMENTS

| | | | | |
|---|---|---|---|---|
| 5,098,443 A | * | 3/1992 | Parel et al. | 623/907 |
| 5,743,274 A | * | 4/1998 | Peyman | A61F 9/00727 128/898 |
| 6,117,170 A | * | 9/2000 | Batdorf, Sr. | 623/4.1 |
| 6,135,118 A | * | 10/2000 | Dailey | A61F 9/00727 128/898 |
| 6,197,056 B1 | * | 3/2001 | Schachar | 623/4.1 |
| 2003/0139808 A1 | * | 7/2003 | Shahinpoor et al. | 623/4.1 |
| 2005/0177232 A1 | * | 8/2005 | Ashton | 623/6.63 |
| 2010/0234862 A1 | * | 9/2010 | Patel et al. | 606/151 |

FOREIGN PATENT DOCUMENTS

WO   WO 9406381 A1 * 3/1994 ............... A61F 2/14

* cited by examiner

*Primary Examiner* — David H Willse
*Assistant Examiner* — Javier Blanco
(74) *Attorney, Agent, or Firm* — Daniel S. Polley, P.A.

(57) ABSTRACT

The novel design of the one piece self-locking scleral buckle eliminates the need for a separate tire, band and sleeve by incorporating the band with the tire and making the device self-locking so the sleeve is no longer necessary. As one piece of silicone replaces the need for three separate pieces of silicone scleral buckling surgery is simplified thus making the procedure faster, safer and more efficient. The novel design of the scleral buckle placement instrument allows the surgeon to more firmly grasp the silicone material making the procedure faster and more efficient.

3 Claims, 4 Drawing Sheets

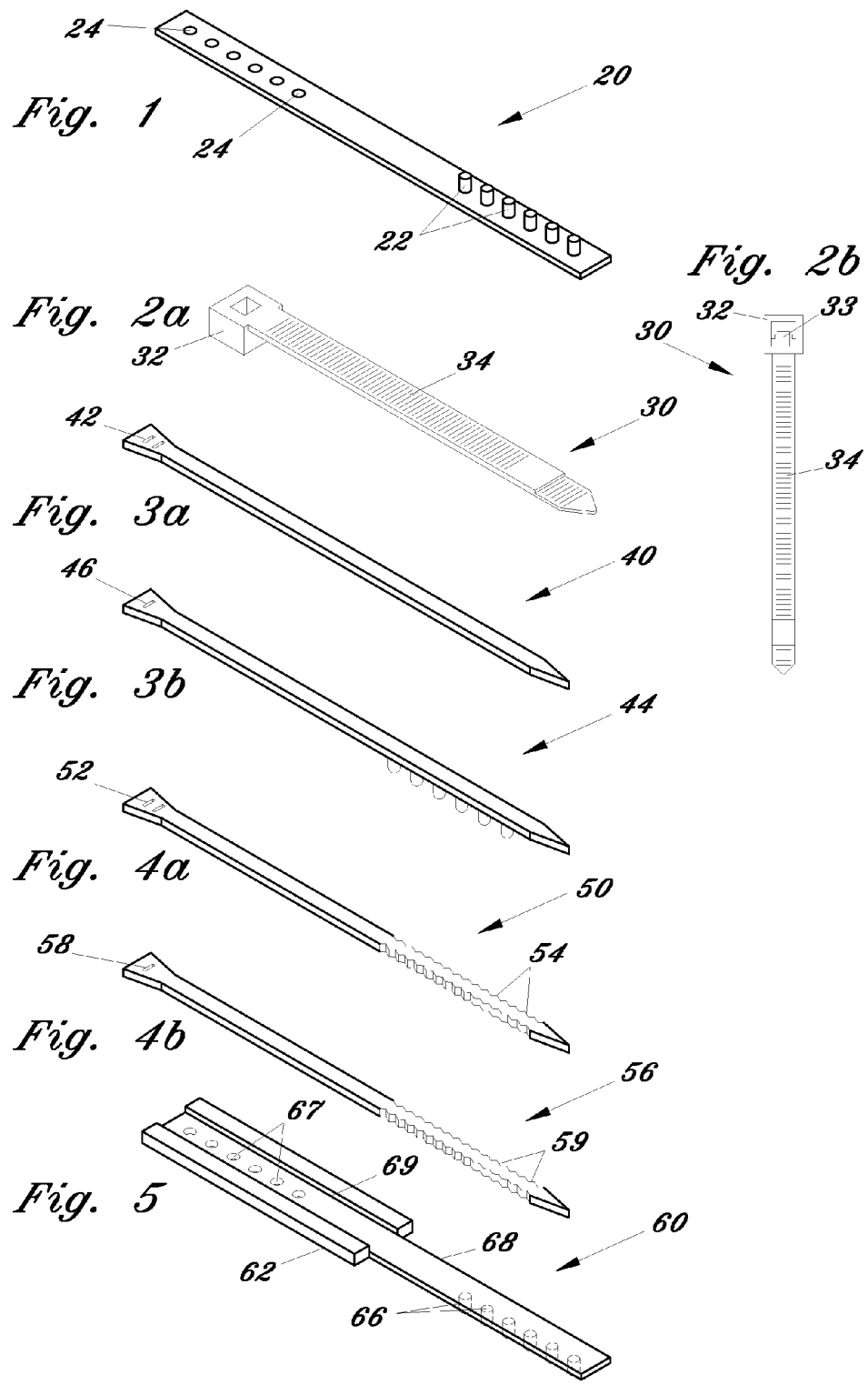

ONE PIECE SELF-LOCKING SCLERAL BUCKLE WITH PLACEMENT INSTRUMENT

This application is a Continuation-In-Part of U.S. application Ser. No. 09/151,423, filed Nov. 10, 1998, which application is incorporated by reference in its entirety. The Applicant also filed Disclosure Document No. 421870 through the Disclosure Program of the U.S. Patent and Trademark Office on Jul. 1, 1997, Disclosure Document No. 421870 is also incorporated by reference in their entirety.

FIELD OF THE INVENTION

This invention relates to medical diagnostic and therapeutic methods and, in particular, to a method for simplifying scleral buckling surgery such that the band and tire are incorporated into one piece, is self-locking, and by using the new placement instrument is more easily placed around the eyeball.

DESCRIPTION OF RELATED ART

Ophthalmic surgeons perform scleral buckling surgery for retinal detachment and when support of the intraocular contents is required. This consists of placing either a hard or soft piece of silicone onto or into the sclera and indenting the scleral surface into the eye. The hard silicone may be relatively narrow or wide and is called a band or tire, respectively. Alternatively, soft silicone may be used which is also referred to as a "silicone sponge". Many ophthalmic surgeons use hard silicone when a more extensive retinal detachment is present and circumferential encircling of the globe with more indentation is required. The silicone sponge is generally used when radial segmental indentation of the scleral surface is required. The hard silicone is more favorably used as there appears to be a smaller chance of infection with the hard versus the soft silicone. The chosen buckling material is threaded under the four rectus muscles. Sutures are placed at designated points on the globe in mattress fashion such that further indentation or buckling of the material into the eye may be accomplished.

The width of the indentation may vary through the selection of different widths and configurations of the buckling material. If a narrow degree of encircling is required than a hard silicone band or a narrow silicone sponge may be placed around the eyeball. The ends of the band may be secured by sutures or by placing the ends through a separate metal clip or a silicone sleeve. The inner diameter of the sleeve is smaller than the width of the band. A special instrument is used to stretch the sleeve and the ends of the band are forced through the open sleeve. The special instrument is then pulled free from the band, causing the sleeve to securely retain the ends of the band. This maneuver is cumbersome and difficult. The ends of the soft silicone sponge are generally secured by sutures.

If a broader buckle is required then the surgeon traditionally uses a silicone band which fits within the broader silicone tire. As the tire is not connected to itself a silicone band is used which fits within the tire. The ends of the band are then secured to itself as described above. As the band is not connected to the tire, the placement of the band around the eyeball may prove cumbersome as it too may have to be individually placed under the rectus muscles and sutures. Silicone tires of various widths and configurations may be used to achieve the desired buckling affect. Once the desired buckling affect is achieved, the redundant end or ends of the excess material of the silicone tire and band are trimmed.

As seen in FIG. 14, three silicone items (tire 172 having a groove 174, band 176 and sleeve 178) are required for the buckle 170. With three separate items, there is an increased risk of infection and an increase in the difficulty of the procedure for the surgeon and assisting personnel. The purchasing of three components also increases the time, expense and difficulty of ordering and stocking multiple supplies.

In addition, the presently existing hand-held instruments used to place the buckling material around the eyeball do not easily and adequately hold the material firmly.

BRIEF SUMMARY OF THE INVENTION

The present invention generally provides a one-piece, self-locking scleral buckle, preferably for use in live human scleral buckling surgery. However, the invention can also be used with cadavers or non-human teaching models as well for educational purposes, as well as for veterinary uses. In a preferred embodiment the components or functions of the silicone band and silicone tire can be incorporated or formed into a one piece member and the combined device is self-locking thus eliminating the need for a separate attachment mechanism. It is estimated that in the preferred embodiments, the length of the bands and tires vary approximately from about 3 cm to about 13 cm (and any number/dimension therebetween) and the widths vary from approximately 3 mm to approximately 20 mm (and any number/dimension therebetween) depending on the degree of buckling effect desired. However, these dimensions are not considered limiting and other ranges and values are considered within the scope of the invention. Once the desired tension is achieved, the redundant end of the excess material can be cut and removed thus leaving the locking mechanism intact.

While silicone elastomers Q7-4735 and Q7-4750 (Dow-Coming Corporation, Midland, Mich.) are suggested for the material because of its ease of fashioning, elasticity and strength, it is apparent that other silicone elastomers, blends or materials may be used to achieve the desired purpose and are also considered within the scope of the invention. However, the selected material preferably is able to maintain its strength and elasticity to function as a self-locking scleral buckle material.

A unique hand-held instrument can be provided that aids in the placement of the buckling material around the eyeball. Thus, the present invention provides for an improved technique for the performance of scleral buckle surgery, preferably using a one-piece scleral band or scleral buckle that eliminates the need for multiple pieces. The present invention by its preferred configuration and method of attachment, can comprise both a self-locking scleral band and a scleral buckle. A hand-held instrument that firmly grasps and holds the buckle material for placement around the eyeball is also disclosed.

BRIEF DESCRIPTION OF THE SEVERAL VIEWS OF THE DRAWINGS

FIG. 1 is a perspective view of a first embodiment of the self-locking band in accordance with the present invention;

FIG. 2a is a perspective view of a second embodiment of the self-locking band in accordance with the present invention;

FIG. 2b is a top view of the self-locking band shown in FIG. 2a illustrating the engaging clip;

FIG. 3a is a perspective view of a third embodiment of the self-locking band in accordance with the present invention, having a plurality of apertures;

FIG. 3b is a perspective view of the third embodiment of the self-locking band in accordance with the present invention, having a single aperture;

FIG. 4a is a perspective view of a fourth embodiment of the self-locking band in accordance with the present invention, having a plurality of apertures;

FIG. 4b is a perspective view of the fourth embodiment of the self-locking band in accordance with the present invention, having a single aperture;

FIG. 5 is a perspective view of a fifth embodiment of the self-locking band in accordance with the present invention;

DETAILED DESCRIPTION OF THE INVENTION

Figure 6:
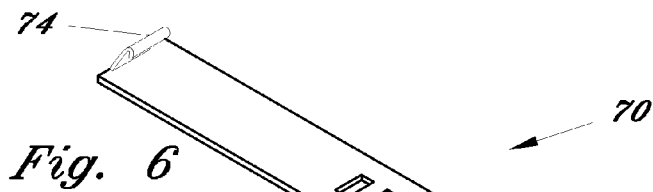
FIG. 6 is a perspective view of a sixth embodiment of the self-locking band in accordance with the present invention.

FIG. 1 illustrates the first buckle embodiment for a scleral buckle in accordance with the present invention and can include a band or tire 20, depending on the width, having at least one, and preferably a plurality of apertures 24 which mate with corresponding pegs 22 for locking a first end of band 20 to a second end of band 20. Self-locking band 20 can be preferably constructed from silicone, though other known or later developed materials can be used and are considered within the scope of the invention.

A bottom surface of this embodiment of the buckle (i.e. the side where the prongs or pegs stick out or protrude upward) can be slightly curved and preferably made rough in texture so that it adheres to the sclera surface without moving. In view of the preferred rough texture, the buckle may be placed under the recti muscles and fixed or retained in place without the use of any sutures or belt loops in the sclera normally used to fix the buckle in place.

Additionally or alternatively, ridges or prongs can be provided that protrude outward from the buckle (such as, but not limited to, the bottom of the buckle), which can be used to hold the buckle in place on the scleral surface. A top portion of the buckle, which can be the side free of locking prongs/pegs 22, can be substantially flat or planar so it doesn't protrude from the scleral surface into the conjunctival tissue.

When band 20 is placed around the eyeball, the appropriate peg 22 is placed within an associated opening 24 such that the desired tension is maintained. Opening 24 can extend through the entire band or a portion thereof (where it would be a recess or cavity as opposed to a opening). Though it is preferred that a plurality of openings 24 and pegs 22 be provided, it is also within the scope of the invention that multiple openings and a single peg or a single opening and multiple pegs be provided on band 20, or even a single opening and single peg can be provided and is considered within the scope of the invention. In all embodiments of the present invention, the pegs should preferably face toward the eye, when the buckle is properly attached around the eye.

Though trimming of an excess portion of the buckle is possible, it is not necessary, as the entire buckle and its overlapping portions can provide more of a buckling effect (in view of the increased thickness) and can be positioned over the retinal tear that caused the detachment.

A basic tenet of scleral buckling surgery is to close the retinal break by indenting the sclera. Overlapping the ends of the buckle over the site of the retinal break can produce an increase in the amount of indentation as compared to the areas indented by a single piece of material. This novel manner of obtaining an increase in indentation does not rely on sutures to produce the additional scleral indentation. The preferred non-smooth underside of the buckle, which can be achieved by roughening the underside, supplying grooves, indentations, prongs, other objects, etc. aids in maintaining the position of the buckle at the same anterior-posterior location on the sclera. In traditional scleral buckling surgery the scleral buckle is placed under the recti muscles and held in place by sutures or passed through belt loops fashioned in the sclera to prevent the buckle from sliding posteriorly. Applicant's novel invention is designed to help prevent posterior sliding without the use of sutures or belt loops.

FIGS. 2a and 2b illustrate another buckle embodiment of the present invention wherein a band 30 is provided having a portion thereof serrated or grooved at 34 and a locking mechanism 32 disposed at an opposite end of band 30. The serrated end of band 30 fits through locking mechanism 32. The orientation of the serrations or grooves allows band 30 to be pulled tighter, but not loosen. The serrated end of band 30 can be tapered to aid in the placement of such end through the locking mechanism 32. Again, with this embodiment, as well as all other embodiments of the present invention, band 30 is preferably constructed from a silicone material. The locking attachment 32 can be a clip 33 (FIG. 2b) at one end of the band such that the serrations or grooves 34 are engaged by clip 33 and retained. In lieu of serrations or grooves, a plurality of pegs can be provided. The band is tightened until the desired tension is achieved. The pegs, serrations or grooves 34 are preferably disposed on a portion of the underside of band 30.

FIG. 3 is another buckle embodiment of the present invention in that one end of the band 40 (FIG. 3a) or 44 (FIG. 3b) is flared and contains with one or more slits or holes 42 (FIG. 3a) or 46 (FIG. 3b) disposed at the flared end. The other end of band 40 or 44 may be placed through the appropriate slit 42 or 46 and locked in place. The non-flared end of band 40 can be preferably tapered such that it may easily be placed through the appropriate slit 42 or 46. Slits 42 and 46 are preferably slightly wider than the tip of the tapered end but smaller than the width of band 40 or 44 such that once the tapered end is pulled through the slit 42 or 46, band 40 or 44 will not slip out. The underside of the band 40 or 44 may be smooth, grooved, serrated or have pegs to aid in locking.

FIG. 4 is another buckle embodiment for the present invention and includes a band 50 or 56 having a flared end with two slits 52 (FIG. 4a) or a single slit 58 (FIG. 4b) disposed at the flared end. The other end of band 50 or 56 may be placed through the appropriate slit or hole 52 or 58 and locked in place. The non-flared end of band 50 or 56 is preferably tapered and contains serrations or grooves 54 or 59, so that the non-flared end may be easily placed through slit 52 or 58. Slits 52 and 58 are preferably slightly smaller than the tapered section of band 50 and 56, such that once the tapered end is pulled through slit 52 or 58 and the serrations or grooves are engaged, band 50 or 56 will not slip out and the desired tension is maintained. The underside of band 50 or 56 may also contain pegs, grooves or serrations to increase the locking ability.

Though FIGS. 3a, 3b, 4a and 4b illustrate a single slit or two slits, it should be understood that such is not limiting and other number of slits can be provided and are considered within the scope of the invention.

FIG. 5 is another buckle embodiment of the present invention and includes a one-piece buckle 60 having band 68 constructed integral with a tire 62 such that a wider buckling effect is achieved. The undersurface of band 68 contains pegs 66 that are placed within holes 67 disposed in tire 62, for achieving the desired tension. Tire 62 defines a groove 69. Similar to the embodiment shown in FIG. 1, pegs 66 are disposed within corresponding holes 67 when properly positioning buckle 60 around an eyeball. The number of holes and pegs provided is not considered limited to any specific number.

FIG. 6 is another buckle embodiment of the present invention in which a tire 70, preferably constructed from silicone, is provided. Tire 70 includes a locking mechanism consisting of a latch 74 which fits within one of a plurality of vertically arranged slits or holes 72.

Figure 7:
FIG. 7 is a perspective view of a seventh embodiment of the self-locking band in accordance with the present invention.

FIG. 7 is another buckle embodiment of the present invention in which a tire 80, preferably constructed from silicone, is provided. Tire 80 includes a locking attachment consisting of a T-shaped bar 82 that fits within one of a plurality of vertically oriented slits or holes 84.

Figure 8:
FIG. 8 is a perspective view of an eighth embodiment of the self-locking band in accordance with the present invention.

FIG. 8 is another buckle embodiment of a tire 90 preferably constructed from silicone. Tire 90 has a locking attachment consisting of a T-shaped bar 92 having a longer support such that bar 92 may be threaded through two vertically oriented slits or holes 94, to increase the security of the lock.

Figure 9:
FIG. 9 is a perspective view of a ninth embodiment of the self-locking band in accordance with the present invention.

FIG. 9 is another buckle embodiment of a tire 100, preferably constructed from silicone, in which a T-shaped bar 102 is placed into one of a plurality of horizontally oriented slits or holes 104 for locking.

Figure 10:
FIG. 10 is a perspective view of a tenth embodiment of the self-locking band in accordance with the present invention.

FIG. 10 is another buckle embodiment in which a tire 110, preferably constructed from silicone, is provided. Tire 110 includes a serrated or grooved end 112 which is placed through at least one of a plurality of horizontally oriented slits or holes 114 for locking purposes.

Figure 11:
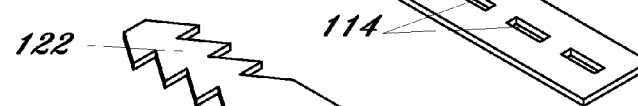
FIG. 11 is a perspective view of an eleventh embodiment of the self-locking band in accordance with the present invention.

FIG. 11 is still another buckle embodiment of a self-locking tire 120, preferably constructed from silicone, in which a serrated or grooved end 122 fits through the desired vertically oriented slit or hole 124 for locking.

It should be understood that the various buckle embodiments for the present invention are not limited to their specific orientation for the slits or holes. Thus, where the slits are shown to be vertically oriented in the drawings, it is also understood and within the scope of the invention that the slits for the same embodiment can also be horizontally oriented. Likewise, where the slits are shown to be horizontally oriented in the drawings, it is also understood and within the scope of the invention that the slits for the same embodiment can also be vertically oriented. It should also be understood that all of the buckle embodiments of the present invention can be provided with either pegs, grooves, serrations, or other attachment mechanisms, and that the various embodiments are not considered limited to any one specific construction. Furthermore, the number or size of the slits, holes, serrations or pegs, for the various embodiments are not considered limited to any specific number or size.

It should also be recognized that the present invention is not limited to silicone as the material for the various buckle embodiments and that other materials may be used and are considered within the scope of the invention.

Figure 12:
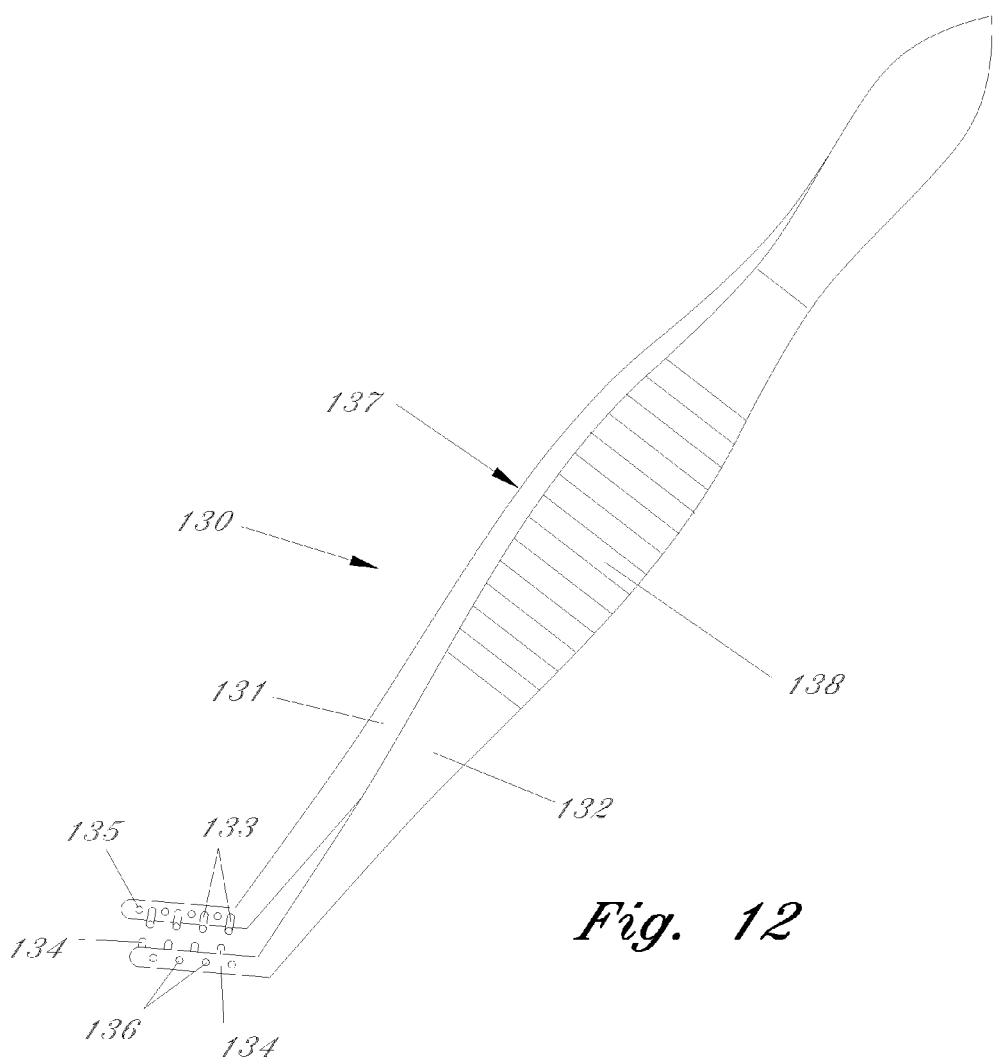
FIG. 12 is a side view of a tool used in accordance with the present invention.

FIG. 12 is a pictorial illustration of a hand-held instrument 130 used to firmly grasp any one of the various buckling embodiments of the present invention. Tool 130 allows for an easier placement of the buckling material around the eye. Tool 130 can also be used with prior art buckles. Tool 130 includes arms 131 and 132, which can be provided with gripping serrations 137 and 138, respectively. Prongs 133 and 134 are provided at one end of the tool to firmly grasp the buckling material to aid in the placement of the buckling material around the globe.

Serrations 137 and 138 provided on the side of instrument 130 aid the surgeon in firmly grasping the instrument. Cavities 135 and 136 can be provided for receiving the tips of prongs 134 and 133, respectively, when not in use. Cavities 135 and 136 also help to prevent dullness of the prongs when handling and/or transporting. Though not limiting, four prongs 133 and 134 and four cavities 135 and 136 are preferably provided. In use, two instruments with right and left angled orientations can be used during the surgical procedure. The instrument may be made from stainless steel, titanium or other materials typically used in ophthalmic surgery.

In use, buckle 142 having a first end with a first locking portion 144 and a second end with a second locking portion 146, in accordance with the various embodiments of the present invention, is placed around an eyeball 140 and under the provided sutures 148 and under the recti muscles 150. Once the buckle is around the eyeball, a surgeon or other individual takes the first end, including locking portion 144, and places it through the locking portion 146 to achieve the desired tension. In all embodiments, the redundant end of the excess buckling material is then cut and removed.

Figure 13:
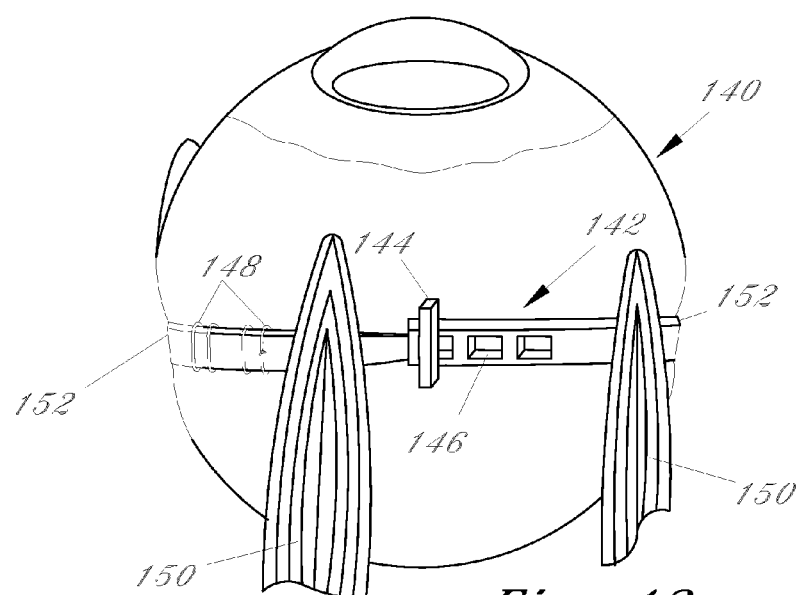
FIG. 13 is a perspective view illustrating the self-locking band of the present invention properly positioned around an eyeball.
Figure 14:
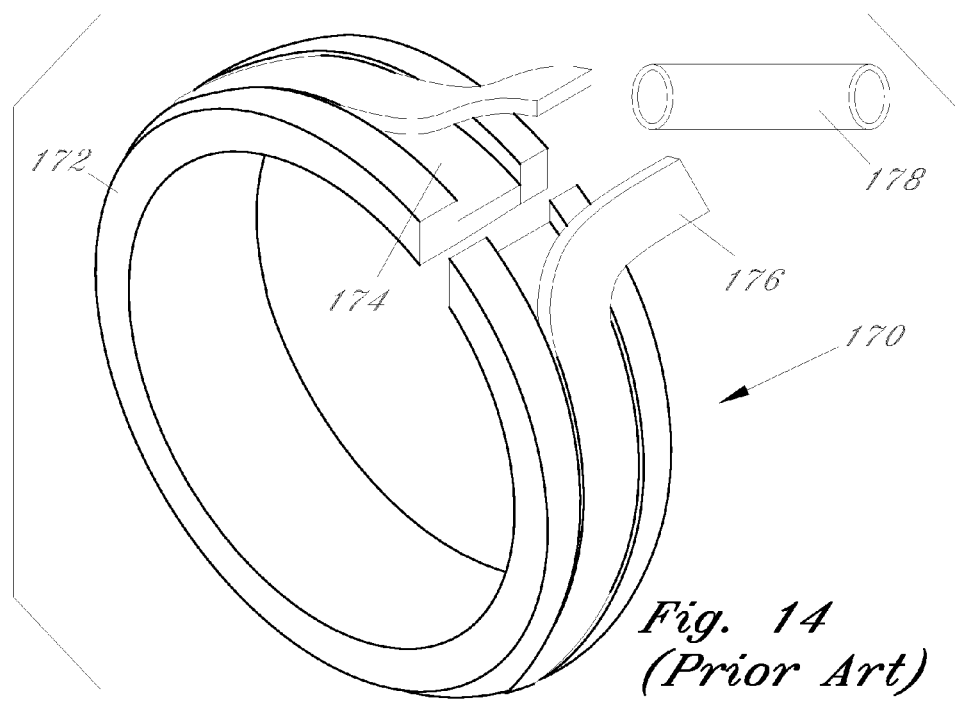
FIG. 14 is a perspective view of a prior art buckle consisting of a separate tire, band and sleeve.

FIG. 13 illustrates the buckle in accordance with the present invention properly disposed around the eyeball and showing indentations 152 of the eyeball. It should be understood that all of the various embodiments of the present invention are similarly disposed around the eyeball and produce indentation of the eyeball.

Changes in modifications within the spirit and scope of the invention will be apparent to those skilled in the art. Such modifications and changes are intended to be covered by the claims herein. For example, the terminology "band" is used for certain width embodiment, whereas the term "tire" is used for larger embodiments. However, these embodiments are not considered limited to any specific width. Thus, the use of the terms "band" or "tire" should not be given any limiting meaning, and it is understood that each embodiment of the present invention can be provided in many different widths.

The scleral buckle of the present invention can be constructed from a non-bioabsorbable or non-absorbable material and/or a biocompatible material. The scleral buckle can also be constructed from a non-metallic material. The buckle can be monolithically formed and/or constructed integral as a one-piece member.

The scleral buckle can be internally connected inside the human body and is preferably used during eye surgery of an eye of a live human being.

In certain embodiments the body member can be provided with a relatively blunt insertion end (not tapered or pointed but rather straight or substantially straight).

In certain embodiments only a single (one) male locking embodiment is provided on the body member and no other male locking members are provided anywhere else on the body member. Also in certain embodiments a first side edge and second side edge have the same or substantially the same width from top to bottom which can also be the same or substantially the same width at the center of the body member.

In certain embodiments, including, but not limited to, the embodiment shown in FIG. 1, the top surface of the scleral buckle can be smooth or substantially smooth and may also be slightly curved or flat to prevent or help to prevent it from eroding through the conjunctival tissue. A roughening of texture and/or ridges, prongs (preferably separate from the locking pegs), etc. may protrude from the underside of the scleral buckle to aid in adhering to the sclera and prevent or help to prevent anterior-posterior slipping of the scleral buckle from the desired location. The underside of the scleral buckle can be curved to aid in indenting the scleral surface and to prevent or help to prevent slippage of the scleral buckle from the desired location. Preferably, the curve in the underside could be greater than the curve of the top surface.

In certain embodiments where a T-shaped male locking member is provided the lengths of the portions that make the T shape can be the same or substantially the same.

All measurements, amounts, sizes, shapes, percentages, configurations, securement or attachment mechanisms, sensing members, sealing members, numbers, ranges, frequencies, values, percentages, materials, orientations, methods of manufacture, etc. discussed above or shown in the drawing figures are merely by way of example and are not considered limiting and other measurements, amounts, sizes, shapes, percentages, configurations, securement or attachment mechanisms, sensing members, sealing members, numbers, ranges, frequencies, values, percentages, materials, orientations, methods of manufacture, etc. can be chosen and used and all are considered within the scope of the invention.

Furthermore, one or more features or characteristics discussed for one embodiment of the present invention can also be used with another of the above discussed embodiments of the present invention.

Unless feature(s) or characteristic(s) described in the specification or shown in the drawings for a claim element or claim term specifically appear in the claim with the claim element or claim term, then the inventor does not considered such feature(s) or characteristic(s) to be included for the claim element or claim term in the claim when and if the claim element or claim term is interpreted or construed.

While the invention has been described and disclosed in certain terms and has disclosed certain embodiments or modifications, persons skilled in the art who have acquainted themselves with the invention, will appreciate that it is not necessarily limited by such terms, nor to the specific embodiments and modification disclosed herein. Thus, a wide variety of alternatives, suggested by the teachings herein, can be practiced without departing from the spirit of the invention, and rights to such alternatives are particularly reserved and considered within the scope of the invention.

What is claimed is:

1. A method for providing a one-piece scleral buckle around an eyeball for fixing or prevent a retinal detachment, the eyeball being associated with recti muscles, said method comprising the steps of:
    (a) providing a one-piece scleral buckle comprising an elongated body member having a substantially rectangular cross-section and having a first end, a second end, a top surface, an underside surface, a first attachment portion beginning at the first end and monolithically formed therewith, and a second attachment portion beginning at the second end and monolithically formed therewith, the first attachment portion having a plurality of apertures extending through the elongated body member, the second attachment portion having a plurality of pegs protruding upward from the underside surface of the elongated body member, the underside surface having a rough texture surface and curved in shape to help prevent slippage of the scleral buckle from its position around an eyeball;
    (b) wrapping the one-piece scleral buckle around an eyeball and positioning the second end over the first end, wherein the rough texture surface directly contacts the eyeball;
    (c) positioning any overlapping portion of said first end and said second end of said buckle over a retinal tear of the eyeball;
    (d) indenting the sclera by self-locking the sclera buckle around the eyeball to a desired tension around the eyeball;
    (e) inserting each of the plurality of pegs into a corresponding one of the plurality of apertures to lock the first attachment portion to the second attachment portion and maintain the desired tension around the eyeball and maintain indentation of the sclera; and
    (f) trimming any excess portion of the scleral buckle not needed for maintaining the self-locking and tension of the scleral buckle around the eyeball;
    wherein self-locking occurs through attaching the first attachment portion of said buckle to the second attachment portion of said buckle,
    wherein said elongated body member forms a substantially circular shape when locked, the substantially circular shape of said elongated body member configured to create and maintain a desired buckling or indentation of the sclera of the eyeball.

2. The method for providing a one-piece scleral buckle around an eyeball of claim 1, wherein said top surface is shaped to help prevent eroding of the buckle through conjunctival tissue.

3. The method for providing a sclera buckle around an eyeball of claim 1, wherein, when the plurality of pegs are inserted into a corresponding one of the plurality of apertures, the plurality of pegs are facing towards the sclera.

* * * * *